United States Patent [19]

Duan et al.

[11] Patent Number: 5,670,097
[45] Date of Patent: Sep. 23, 1997

[54] METHOD OF MAKING BLOOD GAS SENSORS OVERCOATS USING PERMEABLE POLYMERIC COMPOSITIONS

[75] Inventors: Daniel C. Duan, St. Paul; Mark S. Schaberg, Maplewood, both of Minn.; Terence M. Fogarty, Hudson, Wis.; William L. Howard, Jr., Manhattan Beach, Calif.; Kenneth B. Wood, St. Paul, Minn.

[73] Assignee: Minnesota Mining and Manufacturing Company, St. Paul, Minn.

[21] Appl. No.: 351,771

[22] Filed: Dec. 8, 1994

[51] Int. Cl.$^6$ ..................................................... B29D 11/00
[52] U.S. Cl. .................. 264/1.24; 128/637; 264/2.6; 264/232; 264/272.11; 422/68.1; 427/163.2
[58] Field of Search .................................. 264/1.1, 1.24, 264/1.6, 232, 233, 2.6, 272.11, 272.15, 272.16; 427/162, 163.2; 385/12; 422/68.1; 128/634, 637

[56] References Cited

U.S. PATENT DOCUMENTS

| | | |
|---|---|---|
| 3,847,822 | 11/1974 | Shuey . |
| 3,954,475 | 5/1976 | Bonham et al. ........................ 96/67 |
| 4,003,707 | 1/1977 | Lubbers et al. . |
| 4,024,871 | 5/1977 | Stephenson . |
| 4,100,309 | 7/1978 | Micklus et al. . |
| 4,212,970 | 7/1980 | Iwasaki . |
| 4,279,795 | 7/1981 | Yamashita et al. . |
| 4,410,561 | 10/1983 | Hart, Jr. ............................... 427/163.2 |
| 4,557,900 | 12/1985 | Heitzmann ............................ 422/55 |
| 4,642,267 | 2/1987 | Creasy et al. ........................ 428/413 |
| 4,657,736 | 4/1987 | Marsoner et al. .................... 422/56 |
| 4,662,307 | 5/1987 | Amos et al. .......................... 427/163.2 |
| 4,720,343 | 1/1988 | Walch et al. ......................... 210/500.28 |
| 4,758,298 | 7/1988 | Goorsky et al. ...................... 264/1.28 |
| 4,798,847 | 1/1989 | Roesink et al. ...................... 521/50 |
| 4,824,789 | 4/1989 | Yafuso et al. . |
| 4,828,583 | 5/1989 | Oxman et al. . |
| 4,842,783 | 6/1989 | Blaylock ............................... 264/1.27 |
| 4,906,375 | 3/1990 | Heilmann ............................. 210/500.23 |
| 4,934,369 | 6/1990 | Maxwell . |
| 5,056,520 | 10/1991 | Tomisaka et al. .................... 264/1.25 |
| 5,075,127 | 12/1991 | Yafuso et al. . |
| 5,079,272 | 1/1992 | Allegrezza, Jr. et al. ............ 521/134 |
| 5,081,041 | 1/1992 | Yafuso et al. . |
| 5,158,721 | 10/1992 | Allegrezza, Jr. et al. . |
| 5,166,990 | 11/1992 | Riccitelli et al. .................... 128/637 |
| 5,236,969 | 8/1993 | Kunzler et al. ...................... 523/108 |
| 5,333,609 | 8/1994 | Bedingham et al. ................. 128/637 |
| 5,403,746 | 4/1995 | Bentsen et al. . |

FOREIGN PATENT DOCUMENTS

| | | |
|---|---|---|
| 0 601 816 | 6/1994 | European Pat. Off. . |
| 58-16163 | 3/1983 | Japan ................................... 264/1.24 |

OTHER PUBLICATIONS

"Optical Fluorescence and Its Application to an Intravascular Blood Gas Monitoring System", John L. Gehrich et al., *IEEE Transactions on Biomedical Engineering*, vol. BME–33, No. 2, Feb. 1986, pp. 117–132.

"The role of stasis in the clotting of blood and mild flows around soldi objects", John R. E. Christy and Norman Macleod, *Cardiovascular Research*, 1989, 23, 949–959.

PCT Search Report for PCT/US95/14595 (08/351,771).

*Primary Examiner*—Mathieu D. Vargot
*Attorney, Agent, or Firm*—Gary L. Griswold; Walter N. Kirn; F. Andrew Ubel

[57] ABSTRACT

The present invention provides a shaped permeable polymeric material including a hydrophobic portion and a hydrophilic portion, wherein the material is crosslinked. This material is prepared by a method including the steps preparing a crosslinkable composition having a hydrophobic portion and a hydrophilic portion; placing the crosslinkable composition in a mold; gelling the crosslinkable composition to form a shaped gelled polymeric composition comprising a hydrophobic portion, a hydrophilic portion, and a liquid portion; and exchanging the liquid portion with an exchange liquid to form the permeable polymeric material. Preferably this material is used in a blood gas sensor.

39 Claims, 1 Drawing Sheet

METHOD OF MAKING BLOOD GAS SENSORS OVERCOATS USING PERMEABLE POLYMERIC COMPOSITIONS

FIELD OF THE INVENTION

This invention relates to permeable polymeric materials and to a method for preparing these materials. In particular, it relates to polymeric materials suitable for use on sensors used for the testing of liquid samples such as blood, and more particularly, to shaped overcoatings for blood gas sensors.

BACKGROUND OF THE INVENTION

There is a need for a wide range of materials that are permeable to substances dissolved in water and which preferably hold some amount of water. Hydrogels are one type of such material; however, they are somewhat limited. For example, hydrogels generally have limited strength and are often not easy to process into a desired shape. Also, some hydrogel materials cannot stand up to autoclave or steam sterilization. Phase inversion membranes represent another class of materials that hold some amount of water and can be made permeable to substances dissolved in water. However, phase inversion membranes are similarly generally difficult to process into a desired shape. Another class of materials includes membranes that are not naturally permeable but are modified to have a surface porosity that will pass water and water-borne species. These materials also cannot be easily shaped.

Thus, there is a need for materials that are mechanically strong, are permeable to substances dissolved in water, preferably hold water, and can be prepared in any shape desired. The need is particularly acute in medical devices, where it is generally necessary that these materials be relatively unchanged by steam or autoclave sterilization. One application in which such materials would be particularly useful is in fiber-optic-based blood gas sensors. Such sensors would be improved if they had a permeable and mechanically strong overcoating that could be shaped in a manner that reduces blood clotting problems.

SUMMARY OF THE INVENTION

The present invention provides a polymeric material that is permeable to water and water-borne species, e.g., $O_2$, $CO_2$, or ions, and can be processed to provide a shaped article. It is particularly advantageous because it can be molded into a shape that reduces blood clotting problems. The polymeric material is relatively strong, preferably with at least about 300 pounds per square inch (psi) (2068 kPa), and more preferably at least about 525 psi (3620 kPa), tensile strength, and holds water, preferably at least about 25 wt-%. In certain preferred embodiments, the polymeric material is also resistant to steam or autoclaving conditions. Thus, the shaped polymeric material of the present invention is useful as an overcoating for use on a fiber-optic-based blood gas sensor. As used herein, a blood gas sensor encompasses a pH sensor and sensors that detect components in blood other than dissolved gases.

The shaped permeable polymeric material of the present invention comprises a hydrophobic portion and a hydrophilic portion, wherein at least a part of the material is crosslinked. The shaped permeable polymeric material is preferably a substantially nonannealed, nonfluorinated, and nonionic material. In certain embodiments, the hydrophobic portion is preferably substantially noncrystalline at room temperature (20°–25° C.). The hydrophobic and hydrophilic portions can be independent and distinct polymeric materials within the final polymeric material. Alternatively, the hydrophobic and hydrophilic portions can be a part of the same molecule, as in a semihydrophilic material. The shaped permeable polymeric material can be crosslinked as a result of either the hydrophobic portion being crosslinked, the hydrophilic portion being crosslinked, or both the hydrophobic and the hydrophilic portions being crosslinked, either separately or together.

The shaped permeable polymeric material is made by a method that can be adapted to large scale production and is reproducible from article to article. This method comprises: preparing a crosslinkable composition comprising a hydrophobic portion and a hydrophilic portion; placing the crosslinkable composition in a mold; gelling the crosslinkable composition to form a shaped gelled composition comprising a hydrophobic portion, a hydrophilic portion, and a liquid portion; and exchanging the liquid portion with an exchange liquid to form a permeable polymeric material. The initial crosslinkable composition can include monomeric materials and/or polymeric materials. During the gelling step, any monomeric materials are generally polymerized.

The hydrophobic and hydrophilic portions within the crosslinkable composition can be either separate materials or a part of the same material. That is, although typically the hydrophobic portion and hydrophilic portion of the composition result from the use of distinct hydrophobic and hydrophilic materials, the portions can result from semihydrophilic polymers. Semihydrophilic polymers have regions that provide hydrophilic characteristics and regions that provide hydrophobic characteristics.

The compositions of the present invention are particularly advantageous because they retain their shape and volume once gelled. That is, once gelled, the compositions of the present invention are free-standing. Thus, they can be shaped using a mold. In contrast, prior art gelled compositions are generally made into flat sheet membranes, fibers, or hollow tubes by casting, spinning, or extruding techniques.

Definitions

"Hydrophobic portion" means a polymeric or monomeric portion of a composition that absorbs less than about 30 wt-% water, preferably less than about 20 wt-% water, more preferably less than about 10 wt-% water (based on the weight of the hydrophobic portion), and most preferably is generally insoluble in water; a monomeric moiety is hydrophobic if a polymer made from it absorbs less than about 30 wt-% water, preferably less than about 20 wt-% water, more preferably less than about 10 wt-% water (based on the weight of the hydrophobic portion), and most preferably is generally insoluble in water;

"Hydrophilic portion" means a polymeric or monomeric portion of a composition that absorbs greater than about 50 wt-% water, preferably greater than about 80 wt-% water, more preferably greater than about 120 wt-% water (based on the weight of the hydrophilic portion), and most preferably is generally soluble in water; a monomeric moiety is hydrophilic if a polymer made from it absorbs greater than about 50 wt-% water, preferably greater than about 80 wt-% water, more preferably greater than about 120 wt-% water (based on the weight of the hydrophilic portion), and most preferably is generally soluble in water;

"Semihydrophilic polymer" means a polymeric material that contains both hydrophobic and hydrophilic moieties;

"Polymer" or "polymeric material" means a homopolymer or a copolymer (i.e., a polymer containing two or more dissimilar monomers); copolymers derived from more than one type of monomer can be either random or block copolymers; as used herein, the term "polymer" includes oligomers (i.e., polymer molecules consisting of only a few monomeric moieties, such as dimers, trimers, and tetramers);

"Shaped article" or "shaped material" means an article or material that is shaped using a mold that allows for formation of a self-supporting or free-standing three-dimensional shape, rather than a flat membrane sheet, a fiber, a rod, or a hollow tube, which are prepared by solvent casting or dipping, spinning, or extruding;

"Gelled composition" means a self-supporting (i.e., shape retaining) material comprising a crosslinked polymeric portion and a liquid portion;

"Crosslinking agent" means a compound which connects polymer molecules;

"Sensitizer" means a material that absorbs radiant energy and transfers energy to a different material; and "Initiator" means a material that has the ability to produce reactive species, such as radicals, that initiate polymerization and/or crosslinking; a photoinitiator produces radicals upon exposure to light and a thermal initiator produces radicals upon exposure to heat; certain initiators can also function as crosslinking agents.

DETAILED DESCRIPTION OF THE INVENTION

Figure 1:
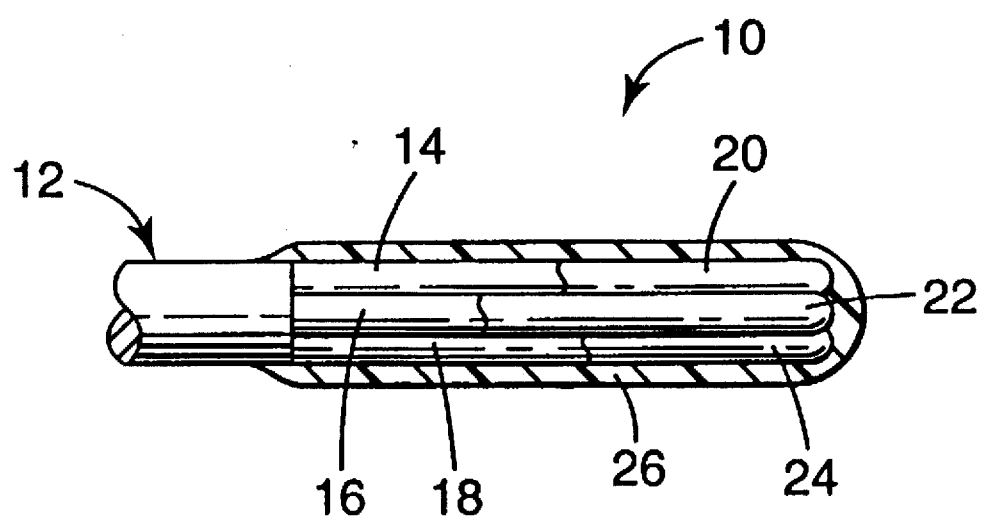
FIG. 1 is a perspective view of a blood gas sensor coated with a permeable polymeric material according to the present invention.

The present invention provides a shaped permeable polymeric material comprising a hydrophobic portion and a hydrophilic portion, wherein at least a part of the polymeric material is crosslinked. It is preferably a substantially nonannealed, nonfluorinated, and nonionic material. It is also preferably resistant to steam or autoclaving conditions. Although such materials can be used for a variety of applications, they are preferably used in overcoatings for blood gas sensors.

Preferably, the shaped polymeric material is permeable to nonionic molecules (such as $CO_2$, $O_2$, small organic molecules having a molecular weight of less than about 500, such as glucose), and more preferably to both nonionic and ionic molecules (such as $H_3O^+$, $OH^-$, $Cl^-$, $Ca^{2+}$, $Na^+$, $K^+$, $HCO_3^-$, $CO_3^{2-}$) that are typically dissolved or dispersed in blood. Of the nonionic molecules, preferably, the shaped polymeric materials are permeable to oxygen, more preferably to oxygen and carbon dioxide, and most preferably to oxygen, carbon dioxide, and glucose. Of the ionic molecules, preferably, the shaped polymeric materials are permeable to hydrogen ions and their counterions, more preferably to ions typically present in blood. It should be understood, however, that to be within the scope of the present invention, the shaped polymeric material need not be permeable to all molecules under all conditions. For use as an overcoating for a blood gas sensor, it is particularly preferred that the shaped polymeric material be permeable to oxygen, carbon dioxide, and the ions typically present in blood.

To determine permeability, a polymeric material of the present invention can be used to overcoat a blood gas sensor and tested for response time. As used herein, "response time" is the time necessary for a concentration dependent signal to reflect the concentration of the analyte of interest in a medium at 37° C. This is determined by exposing the sensor to a first medium containing the analyte of interest and allowing it to equilibrate, and then transferring the sensor to a second medium containing the same analyte, wherein the concentration of the analyte in both mediums is within the operating region of the sensor. The response time includes any time necessary for the sensor to stabilize to the second medium. For this determination of permeability, the media containing the analyte of interest is water. A polymeric material is permeable if a sensor overcoated with a fully hydrated coating of the material (having a coating thickness between about 0.00254 mm and about 0.15 mm as determined by the shortest distance from the outer surface of the sensor element to the outside surface of the coating) increases the response time of the sensor by no greater than about 30 minutes, wherein the same sensor with no overcoating has a response time of no greater than about 1.5 minutes. Preferably, the polymeric materials of the present invention increase the response time of the sensor by no greater than about 10 minutes, and more preferably by no greater than about 2 minutes.

The shaped permeable polymeric material of the present invention preferably has a tensile strength of at least about 300 psi (2068 kPa) in its fully hydrated state when tested as described in Example 2. If used in a blood gas sensor, the tensile strength is more preferably at least about 525 psi (3620 kPa), and most preferably at least about 650 psi (4482 kPa). In particularly preferred embodiments the tensile strength is at least about 800 psi (5516 kPa). The final product, i.e., the shaped permeable polymeric material formed subsequent to gelling and exchanging, preferably holds at least about 25 wt-% water, based on the total weight of the fully hydrated material. More preferably, it holds about 25–70 wt-% water, and most preferably about 35–55 wt-% water, based on the total weight of the fully hydrated material. As used herein, a "fully hydrated material" refers to a material that has been in contact with an aqueous medium, e.g., water or a buffer, for at least about 8 hours at room temperature (20°–25° C.). Also, it preferably can be dried and rehydrated. If it is dried, it can preferably be rehydrated to at least about 70%, more preferably to at least about 90%, and most preferably to at least about 95%, of its original water content (percentages based on weight). If it is to be used as an overcoating for blood gas sensors, it is particularly preferred that the shaped polymeric material be biocompatible and biostable for the duration of the procedure in which the sensor is used.

As stated above, the shaped permeable polymeric material includes a hydrophobic portion and a hydrophilic portion. The hydrophobic portion is used to enhance the physical strength and control the amount of water absorbed by the final product. In certain embodiments, the hydrophobic portion is preferably substantially noncrystalline at room temperature (20°14 25° C.). By this it is meant that the hydrophobic portion has preferably less than about 20%, more preferably less than about 10%, and most preferably less than about 5%, crystallinity as determined by wide-angle x-ray scattering. The hydrophilic portion is used to enhance the permeability, surface wetting, and biocompatibility of the final product. When added to the initial crosslinkable composition, the hydrophobic portion and hydrophilic portion can be present as either monomers or polymers. They can be either separate and distinct materials or a part of the same material, as in a semihydrophilic polymer. Upon gelling, the monomers (and any oligomers present) are typically polymerized. Also during the gelling step, at least a portion of the crosslinkable composition is crosslinked.

In the gelled composition, as well as in the final product, the hydrophobic and hydrophilic portions can be crosslinked independently or the hydrophobic portion can be crosslinked to the hydrophilic portion. Alternatively, only the hydrophobic portion or only the hydrophilic portion can be crosslinked. The only requirement of the shaped permeable polymeric materials of the present invention is that there is some crosslinking within the material. Thus, the shaped gelled composition or the shaped permeable polymeric material can include crosslinked hydrophobic polymer molecules, crosslinked hydrophilic polymer molecules, crosslinked hydrophobic-hydrophilic polymer molecules, or a combination thereof. The crosslinking contributes to the strength and dimensional stability of both the gelled and final material such that they can be handled with substantial retention of shape and size during both processing and use. The crosslinking also contribute to the control of phase behavior. In certain preferred embodiments, the shaped permeable polymeric material of the present invention comprises a crosslinked hydrophilic portion and a non-crosslinked hydrophobic portion.

The initial crosslinkable compositions can include: (1) at least one kind of semihydrophilic polymeric material; (2) at least one kind of hydrophobic monomeric material and at least one kind of hydrophilic monomeric material; (3) at least one kind of hydrophobic polymeric material and at least one kind of hydrophilic monomeric material; (4) at least one kind of hydrophobic monomeric material and at least one kind of hydrophilic polymeric material; or (5) at least one kind of hydrophobic polymeric material and at least one kind of hydrophilic polymeric material. These compositions can also include an organic solvent to solvate or disperse the hydrophobic and hydrophilic monomers and/or polymers, if desired. Preferably, the initial crosslinkable composition includes at least one kind of hydrophobic polymeric material and at least one kind of hydrophilic monomeric material.

As stated above, once gelled, the majority of the monomeric material (or oligomeric material) used is generally polymerized. Also, the gelled material is crosslinked to at least some extent. The resultant shaped gelled composition includes a hydrophobic portion, a hydrophilic portion, and a liquid portion that is capable of being exchanged with an exchange liquid. The liquid portion can be unpolymerized monomeric material, noncrosslinked hydrophilic polymer, an organic solvent used to prepare the composition, or mixtures thereof. Preferably, the liquid portion of the gelled composition is a solvent used to solvate or disperse the hydrophobic and hydrophilic monomers and/or polymers in the crosslinkable composition.

Suitable hydrophobic polymers include, but are not limited to, polysulfones, polyethersulfones, polyarylsulfones, polyimides, polyarylates, cellulose acetates, polyurethanes, polycarbonates, polyester carbonates, acrylonitrile polymers, phenoxy resins, silicones, polyether imides, cellulose acetate butyrates, nylons, polyvinyl butyrals, polyarylene oxides such as polyphenylene oxide, i.e., poly(2, 6-dimethyl-p-phenylene oxide), poly(urea urethane)s, polyphenyl quinoxalines, and mixtures thereof. Of these, polyurethanes and poly(urea urethane)s are preferred. Suitable hydrophobic monomers include, but are not limited to, benzyl acrylate, benzyl methacrylate, phenyl acrylate, phenyl methacrylate, styrene, methyl methacrylate, urethane acrylates, acrylonitrile, norbornyl acrylate, and mixtures thereof. Of these, phenyl and benzyl (meth)acrylates are preferred. In the crosslinkable compositions in which the hydrophobic polymers or monomers are present, they are present in an mount effective to provide a final product with the strength and water absorption characteristics required for the desired product.

Suitable hydrophilic polymers include, but are not limited to, poly(N-vinyl pyrrolidone), poly(N,N-dimethyl acrylamide), poly(N-vinyl-N-methyl acetamide), poly(N-vinyl valerolactam), poly(acrylamide), poly(acrylic acid), poly(hydroxy ethyl acrylate), poly(hydroxy ethyl methacrylate), poly(ethylene oxide), poly(propylene oxide), poly(vinyl alcohol), as well as ethylenically unsaturated versions of these polymers, and copolymers or mixtures thereof. Of these, poly(N-vinyl pyrrolidone), poly(N,N-dimethyl acrylamide), and poly(N-vinyl-N-methyl acetamide) are preferred. Suitable hydrophilic monomers include, but are not limited to, N-vinyl pyrrolidone, N,N-dimethyl acrylamide, N-vinyl-N-methyl acetamide, N-vinyl valerolactam, N-vinyl caprolactam, acrylamide, acrylic acid, hydroxy ethyl acrylate, hydroxy ethyl methacrylate, poly (ethylene glycol) methyl ether acrylate, and mixtures thereof. Of these, N-vinyl pyrrolidone, N,N-dimethyl acrylamide, and N-vinyl-N-methyl acetamide are preferred. In the crosslinkable compositions in which the hydrophilic polymers or monomers are present, they are present in an mount effective to provide a final product with the permeability and water absorption characteristics required for the desired product.

Suitable semihydrophilic polymers include, but are not limited to, hydrophilic polyurethanes, N-vinyl pyrrolidone copolymers, N,N-dimethylacrylamide copolymers, vinyl alcohol copolymers, N-vinyl-N-methyl acetamide copolymers, acrylamide copolymers, acrylic acid copolymers, hydroxy ethyl acrylate copolymers, hydroxy ethyl methacrylate copolymers, hydrophilic block/ hydrophobic block-block or graft polymers, as well as ethylenically unsaturated versions of these polymers.

The crosslinkable compositions of the present invention can also include an organic solvent. The particular solvent employed will depend on the particular polymeric and/or monomeric components. Suitable organic solvents are those that can dissolve or disperse both the hydrophobic components and the hydrophilic components as well as any optional crosslinking agents or other additives in the amounts used. Suitable organic solvents include, but are not limited to, N-methyl pyrrolidone, N,N-dimethyl formamide, and N,N-dimethylacetamide. A solvent is used in an amount effective to solubilize or disperse the components.

Preferably, hydrophobic polymers or monomers are present in the crosslinkable compositions in an amount of about 10–70 wt-%, more preferably about 10–40 wt-%, and most preferably about 20–35 wt-%, based on the total weight of the crosslinkable composition. Preferably, hydrophilic polymers or monomers are present in the crosslinkable compositions in an amount of about 590 wt-%, more preferably about 10–65 wt-%, and most preferably about 20–45 wt-%, based on the total weight of the crosslinkable composition. More specifically, in crosslinkable composition (1), the semihydrophilic polymer is present in an amount of about 40–70 wt-%, based on the total weight of the composition. In crosslinkable composition (2), the total content of the monomeric material is preferably about 40–70 wt-%, with the amount of hydrophobic monomeric material to hydrophilic monomeric material present in a ratio of about 0.5:1 to 1:1. In crosslinkable composition (3), the hydrophobic polymeric material is preferably present in an amount of about 10–40 wt-%, more preferably about 20–35 wt-%, and the hydrophilic monomeric material is preferably present in an amount of about 10–90 wt-%, more preferably about 10–65 wt-%, and most preferably about 20–45 wt-%. In crosslinkable composition (4), the total content of the monomeric and polymeric material is preferably about 40–70 wt-%, with the amount of hydrophobic monomeric material to hydrophilic polymeric material present in a ratio of about 0.5:1 to 1:1. In crosslinkable composition (5), the total content of the polymeric material is preferably about 15–70 wt-%, more preferably about 30–60 wt-%, with the amount of hydrophobic polymeric material to hydrophilic polymeric material present in a ratio of about 0.5:1 to 1:1.

The gelling process of the method of the present invention involves crosslinking hydrophobic and/or hydrophilic portions of a composition. crosslinking can be carried out by a wide variety of methods. For example, these portions can be crosslinked by the use of a crosslinking agent and/or an initiator, which can optionally be activated by either heat or light. They can also be crosslinked by the use of ionizing radiation, such as e-beam or gamma radiation, without a crosslinking agent or photoinitiator. That is, without the presence of a crosslinking agent or photoinitiator, radicals can be generated in the polymeric portions that can then interact and form a crosslink between the polymeric portions of the composition. Furthermore, reactive groups on the polymer can react and cause crosslinking. It should be understood that a mixture of crosslinking agents and photoinitiators can be used to advantage. Preferred compositions of the present invention are crosslinked using a crosslinker and a photoinitiator.

The crosslinking agents used herein can react with preexisting polymer molecules or become incorporated into a crosslinked polymer during polymerization of monomers or oligomers. Crosslinking agents that are suitable for use in the present invention can be difunctional or multifunctional. They can include, but are not limited to, diallyl maleate, N,N'-methylene bis acrylamide, divinyl succinate, divinyl adipate, divinyl maleate, divinyl oxalate, divinyl malonate, diallyl itaconate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, dimethallyl adipate, diethyleneglycol divinyl ether, butanediol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, butane diol dimethallyl ether, 3,3'-ethylidene bis(N-vinyl-2-pyrrolidone), 1,3-diallyl urea, ethylene glycol diacrylate, ethylene glycol dimethacrylate, diethylene glycol diacrylate, diethylene glycol dimethacrylate, 1,3- and 1,4-butane diol diacrylate, 1,3- and 1,4-butane diol dimethacrylate, tolylene-2,4-diisocyanate, 4,4'-methylene bis(phenyl isocyanate), glyceryl triacrylate, and pentaerythritol tetraacrylate. Particularly preferred crosslinking agents are diallyl maleate, ethylidene bis vinyl pyrrolidone, N,N'-methylene bisacrylamide. A crosslinking agent, when employed, is used in an amount sufficient to achieve the desired extent of crosslinking. Preferably, a crosslinking agent is present in a crosslinkable composition in an amount of about 0.01–30 wt-%, more preferably about 1–30 wt-%, and most preferably about 5–20 wt-%, based on the total weight of the material capable of reacting with the crosslinking agent.

Initiators that are suitable for use in the present invention include, but are not limited to, photoinitiators, such as ultraviolet- or visible-light-induced initiators, or thermal initiators. Examples of suitable ultraviolet-induced initiators include, but are not limited to, ketones such as benzil and benzoin, and acyloins and acyloin ethers commercially available, for example, from Aldrich Chemical Co. Preferred ultraviolet-induced polymerization initiators include 2,2-dimethoxy-2-phenylacetophenone and benzoin methyl ether (2-methoxy-2-phenylacetophenone), both commercially available from Ciba-Geigy Corp., and the photoinitiator DAROCURE 1173 ($C_6H_5C(O)C(OH)(CH_3)_2$), commercially available from EM Chemicals of Hawthorne, N.Y. Examples of suitable visible-light-induced initiators include, but are not limited to, diaryliodonium salts and triarylsulfonium salts, as well as chromophore substituted halomethyl-s-triazines, such as those described in U.S. Pat. No. 3,954,475, and halomethyl oxadiazoles, such as those described in U.S. Pat. No. 4,212,970. Such initiators can be used alone or in combination with suitable accelerators, e.g., amines, peroxides, and phosphorus compounds, and/or with suitable photosensitizers, e.g., ketone or alpha-diketone compounds such as camphorquinone as described in U.S. Pat. No. 4,828,583. For crosslinkable materials that are polymerized by a cationic mechanism, suitable initiators include salts that are capable of generating cations such as diaryliodonium, triarylsulfonium, and aryldiazonium salts. Preferred visible-light-induced initiator systems include suitable combinations of a diketone, e.g., camphorquinone, and a diaryliodonium salt, e.g., diphenyliodonium chloride, bromide, iodide, or hexafluorophosphate, with or without additional hydrogen donors, or accelerators, such as sodium benzene sulfinate, amines, or amine alcohols. Redox initiators can also be used in the method of the present invention as long as they exhibit a desired combination of such properties as stability and efficiency of free-radical production and polymerization. An initiator, when employed, is used in an amount sufficient to achieve the desired extent of polymerization and/or crosslinking. Preferably, an initiator is present in a crosslinkable composition in an amount of about 0.01–10 wt-%, more preferably about 0.5–8 wt-%, and most preferably about 1–5 wt-%, based on the total weight of the material capable of polymerizing and/or crosslinking.

The crosslinkable compositions of the present invention can be cured using a source of radiation of sufficient energy (i.e., wavelength range) to generate free radicals when incident upon the particular initiator selected for use in the composition. The preferable wavelength range is about 500–250 nm.

Minor amounts, i.e., less than about 50 wt-%, of additives can also be included in the compositions for particular advantage, such additives include, for example, additives for preventing blood clotting such as heparin, pigments such as $TiO_2$ and iron oxides, carbon, reinforcing fibers, and nucleating agents such as small particles of polyvinyl alcohol.

During the gelling process, there is preferably substantially no volume change, e.g., contraction of the material, although this is not a necessary requirement. Once gelled, i.e., polymerized (if necessary) and crosslinked, the gelled composition contains a polymer having a hydrophobic portion, a polymer having a hydrophilic portion (which can be the same or different from the polymer having the hydrophobic portion), and a liquid portion. Typically, the liquid portion of the crosslinkable composition serves to occupy volume while the hydrophobic and hydrophilic portions are polymerized (if necessary) and crosslinked. As stated above, the liquid portion can be unpolymerized monomeric or oligomeric material, noncrosslinked hydrophilic polymer, solvent used to prepare the composition, or a mixture thereof. Preferably the liquid portion capable of being exchanged is not noncrosslinked hydrophobic polymer.

Substantially all of the liquid portion is removed from the composition by an exchange process, i.e., one or more steps involving exchanging this liquid portion with an exchange liquid. This results in a stronger material having greater mechanical integrity. This exchanging can occur by any of several methods. For example, a substantial amount of the liquid portion can be removed from the gelled composition by evaporation. Subsequently, an exchange liquid can be added to the gelled composition to replace the evaporated liquid portion. Alternatively, the gelled composition can be exposed to the vapor of an exchange liquid. As another alterative, the gelled composition can be exposed to a humid atmosphere, prior to the exchanging step. This humid atmosphere can be accomplished by exposing the gelled composition to a flow of steam, or simply by exposing the gelled composition to room humidity. Typically, however, an exchange liquid is added to the gelled material, which replaces an approximately equal volume of the liquid portion. Preferably, the exchange process is done in such a manner that the material does not excessively distort or swell. By this it is meant that in preferred embodiments, the exchange process occurs with less than about a 40% change in volume, more preferably less than about a 30% change in volume, and most preferably less than about a 20% change in volume. In certain applications, such as in overcoated blood gas sensors, it is desirable to use a composition that does not substantially distort or swell during the exchange process to avoid the overcoating from fracturing or pulling away from the sensor. It should be understood, however, that a greater amount of volume change can be tolerated for certain applications.

The exchange liquid can be any liquid that is capable of dissolving the liquid portion. Suitable exchange liquids include, but are not limited to, water, methanol, ethanol, isopropanol, acetone, as well as mixtures of these exchange liquids with the solvents listed above. If the liquid is water, this hydrates the finished material, which is desirable. If the liquid is an organic solvent, this can be removed by evaporation and replaced by water or directly exchanged with water to hydrate the finished material.

Shaped articles are prepared using the method of the present invention by placing the crosslinkable composition in a mold prior to the gelling step. An overcoated article, e.g., an overcoated blood gas sensor, can be prepared if a portion of the article to be coated is placed in the mold with the composition. Typically, it is convenient to demold the article before the exchange step is performed, but occasionally applications may occur where it is convenient to perform the exchange step while the article is still in contact with the mold. As will be discussed with more particularity below, in one contemplated use, the article will be an optical fiber or a bundle of optical fibers, each bearing sensor dyes, and the overcoated article will serve as an indwelling arterial blood gas sensor. In some embodiments of such an indwelling sensor, it may be convenient to provide a supporting catheter having one or more lumens to support and introduce the bundle of optical fibers into the artery of the patient. A thermal sensor can also be optionally included in such a bundle. The predetermined shape will be designed to improve hemodynamical flow around that portion so as to minimize the development of blood clots on the sensor which would reduce its sensitivity. In particularly preferred embodiments, because the exchange step occurs with no substantial change in the size or shape of the coating, the method of the present invention allows the composition to be coated or molded on very small and delicate assemblies.

Thus, the method of the present invention involves the steps of preparing a crosslinkable composition comprising a hydrophobic portion and a hydrophilic portion; placing the crosslinkable composition in a mold; gelling the crosslinkable composition to form a shaped gelled polymeric composition comprising a hydrophobic portion, a hydrophilic portion, and a liquid portion; and exchanging the liquid portion with an exchange liquid to form a shaped permeable polymeric material. The exchange process is preferably carried out after the gelled composition is removed from the mold, although this is not always necessary. It can be carded out in one or more steps.

In a particularly preferred embodiment, a solution is prepared using a hydrophobic polymer, a hydrophilic monomer, a crosslinking agent suitable for use with the monomer, and a solvent capable of solvating these components. This composition is placed in a mold. Next, polymerization of the monomer is initiated as well as crosslinking, so as to form a crosslinked gel. This gelling step preferably involves substantially no volume change in going from the crosslinkable composition to the gel, although for some applications this can be tolerated. If there is contraction, however, additional material can be added to the mold or the mold can be overfilled, for example. Typically, the mold is then removed from this gel. This gel is still swelled by the solvent, yet it has some internal cohesion because of the crosslinking. Finally, the solvent in the gel is replaced with a liquid that causes the composition to form a tough, permeable material. Surprisingly, no substantial change of size or shape of the material occurs during this exchange, which makes the composition particularly useful in medical applications where the exchange can be counted on not to interfere with the preparation of the hemodynamically compatibly shaped overcoating of, e.g., a blood gas sensor.

It is also noted that in some cases, superior results are achieved if the gelling step is conducted under an oxygen-reduced environment. This can be accomplished by using an oxygen impermeable mold. Using such a mold, oxygen can be excluded from the surface of the crosslinkable composition. This effectively produces an oxygen-reduced environment. Alternatively, oxygen can be evacuated from the composition and replaced with an inert atmosphere, e.g., nitrogen or argon. An oxygen-reduced environment is particularly necessary if the polymerization process involves the formation of free radicals. Thus, the level of oxygen is preferably reduced to a level such that the polymerization process is not substantially hindered. An oxygen-reduced environment, particularly when created by an oxygen impermeable mold, can increase the surface hydrophilicity of the material.

The mold for preparing the shaped material can be made of a variety of materials. It can be made of metal, glass, quartz, plastics, silicone, etc. It can be machined or injection molded. Preferably, the mold is made of a material that is transparent to the desired gelling radiation, e.g., ultraviolet or visible radiation. If the mold is made of a swellable material, such as silicone, it is preferably presoaked in the composition to be gelled, in one or more components of the composition to be gelled, or in other materials that will swell the mold material. If upon gelling, the crosslinkable material appreciably contracts, and this is not desired for the application of interest, the mold can include a reservoir for adding more crosslinkable material.

The present invention also provides articles having a crosslinked, shaped overcoating, preferably these articles are overcoated blood gas sensors. Referring to FIG. 1, the most distal portion of a blood gas sensor 10 is illustrated. The sensor 10 comprises a fiber optic bundle 12, which in the illustrated embodiment includes fibers 14, 16, and 18. Fiber 14 is coated at the end with a sensor chemistry 20 which is sensitive to the pH in a surrounding aqueous environment, fiber 16 is coated at the end with a sensor chemistry 22 which is sensitive to the concentration of $CO_2$, and fiber 18 is coated at the end with a sensor chemistry 24 which is sensitive to the concentration of $O_2$. The entire distal end is coated with a permeable polymeric material 26 according to the present invention, which has a smooth hydrodynamic shape. In this application, the permeable polymeric material is as thin as possible so that response time is not significantly lengthened. Preferably, the overcoating is about 0.00254–0.15 mm thick. This thickness refers to the shortest distance from the outer surface of the sensor element to the outside surface of the overcoating.

Objects and advantages of this invention are further illustrated by the following examples. The particular materials and amounts thereof recited in these examples as well as other conditions and details, should not be construed to unduly limit this invention. All materials are commercially available except where stated or otherwise made apparent. All parts and percentages used herein are by weight, unless otherwise specified.

EXAMPLE 1

Formation of Films

This example demonstrates the present invention using a hydrophilic monomer (N-vinyl pyrrolidone) and a hydrophobic polymer (polyurethane) with a solvent (N-methyl pyrrolidone). An overcoat precursor solution was prepared by mixing 27 g of N-vinyl pyrrolidone ("NVP", commercially available from Aldrich Chemical Co. of Milwaukee, Wisc.), 21 g of polyurethane (commercially available as TECOFLEX NJ-85A from Thermedics of Woburn, Mass.), 52 g of N-methyl pyrrolidone ("NMP", commercially available from Aldrich), 0.54 g of diallyl maleate (a crosslinker commercially available from Aldrich), and 1.1 g of a polymerization photoinitiator (commercially available as DAROCURE 1173 from EM Chemicals of Hawthorne, N.Y.). This solution was prepared with warming to a temperature of about 40°–50° C. using an IR lamp (the solution was protected from the light, however) to help dissolve the materials in the NMP.

Films were made from the overcoating precursor solution by bar coating at 0.13 mm onto a fluorosilicone release liner and coveting the solution with a 0.03 mm untreated biaxially oriented polypropylene film. This sandwich was then exposed to UV light (275 watt Sunlamp from Sylvania of Danvers, Mass.) and polymerized/crosslinked to form a gel. The film was 12 inches (30.5 cm) from the source, and was irradiated for 45 minutes.

This gelled film was then placed in a bath of 70° C. water to exchange the NMP with water. This procedure was carded out with several other exchange liquids, e.g., room temperature (20°14 25° C.) water, methanol, ethanol, isopropanol, a 85/15 N-methyl pyrrolidone/water mixture, and acetone. The gelled films were exposed to the exchange liquid bath for 2 minutes, and then transferred sequentially to several (typically five) rinsing baths of room temperature (20°14 25° C.) water. Tough, opaque films were obtained.

The film obtained using the 70° C. water exchange method was tested for its water content, which was found to be 59%. The film was then exposed to room temperature (approximately 20°–25° C.) and room humidity (approximately 20–70%) overnight to dry the film. After dry down, this film was rehydrated by putting it in a water bath. It returned to 95% of its original water content.

EXAMPLE 2

Preparation of Overcoated Blood Gas Sensors

Films from the precursor solution of Example 1 were molded on a CDI system 1000 fiber optics based blood gas sensor (obtained from Cardiovascular Systems, Inc., Tustin, Calif.) using the following procedure. A bundle of three optical fibers, each 0.2 mm in diameter, was prepared. Each of the fibers had a fluorescent sensor dye-based composition on its tip, each of which with a variable fluorescence depending on the pH and concentrations of $CO_2$ and $O_2$, respectively, to which it is exposed. These fiber bundles were made generally in accordance with the disclosures of I.E.E.E. Transactions in Biomedical Engineering, 33(2), 117–132 (1986), and U.S. Pat. Nos. 4,003,707, 4,557,900, 4,657,736, 4,824,789, 5,075,127, and 5,081,041. A translucent silicone mold was prepared, having a cylindrical cavity with a rounded end, the cavity having a diameter slightly larger than the fiber optic bundle. This mold was soaked in the precursor solution of Example 1 in order to pretreat it, wiped dry, and charged with the precursor solution of Example 1. The fiber optic bundle of Example 1 was then inserted into the mold to within 0.025–0.05 mm of the cavity end. A polymerization reaction within the mold was initiated by the UV light source described in Example 1, irradiating the mold for 45 minutes at a distance of 12 inches (30 cm). After the irradiation, the mold was chilled in a dry ice/methanol bath. The mold was then cut open to release the gel coated bundle. The gel coated bundle was allowed to reach room temperature and then exposed to a flow of steam for 0.5 minute, and then a bath of deionized water at 70° C. for 5 minutes to exchange the NMP with water. At this point, a tough adherent overcoat had been provided for the bundle.

This overcoated fiber optic bundle was tested as was a similar bundle without an overcoat. This was done by connecting these bundles in turn to a blood gas analyzer generally as described in U.S. Pat. No. 4,934,369, and I.E.E.E. Transactions in Biomedical Engineering, 33(2), 117–132 (1986), irradiating the sensor dyes with exciting radiation, and gauging the fluorescence generated. Two different buffer solutions (commercially available from Ciba Coming Diagnostics of Medfield, Mass.) were provided, one identified as having a pH of 6.838, and the other having a pH of 7.382. The purpose of this test was to evaluate the permeability of the overcoating by testing the response time of the sensor before overcoating followed by the response time of the same sensor overcoated with the compositions described herein to a step change in pH. This was done by placing the sensor in one of the two buffer solutions described above, allowing the sensor to come to equilibrium for at least 60 seconds, and then transferring the sensor to the second of the two buffer solutions and monitoring the change in response of the sensor to the second buffer solution with time. The data in Tables 1–3 resulted from equilibrating the sensors in the 7.382 pH buffer solution and transferring them to the 6.838 pH buffer solution, both solutions at room temperature (20°14 25° C.). The data in Tables 4–7 resulted from equilibrating the sensors in the 6.838 pH buffer solution and transferring them to the 7.382 pH buffer solution, both solutions at 37° C. The response was monitored for 5 minutes and the times required for the sensor to make a 63% change in the signal (τ63) and a 90% change in the signal (τ90) were noted (100% signal change is the difference between the intensity of the signal of the second buffer at the end of the 5 minute period and the intensity of the equilibrated signal of the first buffer). The results are reported in Table 1.

TABLE 1

|  | Time to 63% signal change (seconds) | Time to 90% signal change (seconds) |
|---|---|---|
| Without overcoat | 28 | 40 |
| With overcoat | 172 | 236 |

Although the response time had been increased by the overcoat, it was acceptable for indwelling catheter sensing. For preferred sensors, which are substantially equilibrated (i.e., at about 80% of equilibrium) within 5 minutes, τ90 is no greater than about 250 seconds.

Using this composition, films were prepared as described in Example 1 for tensile testing to determine the strength of the material. The films were placed in 20°–25° C. water to exchange out the liquid portion and then placed in water for storage prior to testing. The hydrated test samples were die punched giving a 0.5 inch (1.27 cm) wide specimen and tested on an MTS® System 880 (Eden Prairie, Minn.) using a hydraulic constant rate of extension. The jaw separation distance was 1 inch (2.54 cm) and the jaw speed was 3 inches per minute (7.6 cm/minute). The jaw faces were smooth and the jaw pressure was 50 psi (345 kPa). The specimens were taken out of water, measured for thickness and immediately tested. The testing was done at room temperature and humidity. Calculations were based on a cross-sectional area of 0.5 inch (1.27 cm) times the measured thickness. The tensile strength of the films made using this composition was 550 psi (3792 kPa) (average of 4 samples).

EXAMPLE 3

This example demonstrates the present invention using a hydrophilic monomer (N,N-dimethyl acrylamide) and a hydrophobic polymer (polyethersulfone) with a solvent (N-methyl pyrrolidone). A solution was prepared by mixing 20% by weight of N,N-dimethyl acrylamide (commercially available from Aldrich Chemical Co.), 30% by weight of polyethersulfone (commercially available as 4100G from ICI Americas of Wilmington, Del.), and 50% by weight of N-methyl pyrrolidone. To this was added 2.5% N,N'-methylene bis acrylamide (a crosslinker commercially available from Aldrich Chemical Co.), and 5% DAROCURE 1173 photoinitiator, both of which were based on the weight of N,N-dimethyl acrylamide. This precursor solution was prepared with warming to a temperature of about 40°–50° C. using an IR lamp (the solution was protected from the light, however) to help dissolve the materials in the N-methyl pyrrolidone.

Fiber optic bundles were prepared according to Example 2 using this overcoating precursor solution. The overcoated bundles were then tested according to the method of Example 2. The results are listed in Table 2.

TABLE 2

|  | Time to 63% signal change (seconds) | Time to 90% signal change (seconds) |
|---|---|---|
| Without overcoat | 38 | 70 |
| With overcoat | 174 | 238 |

EXAMPLE 4

This example demonstrates the present invention using a hydrophilic monomer (N-vinyl pyrrolidone) and a hydrophobic polymer (polyurethane) with a solvent (N-methyl pyrrolidone). A solution was prepared by mixing 20% by weight of N-vinyl pyrrolidone, 30% by weight of polyurethane (commercially available as ESTANE 5701 from B. F. Goodrich of Cleveland, Ohio), and 50% by weight of N-methyl pyrrolidone. To this was added 2.5% diallyl maleate (a crosslinker commercially available from Aldrich Chemical Co.), and 5% DAROCURE 1173 photoinitiator, both of which were based on the weight of N,N-dimethyl acrylamide. This precursor solution was prepared with warming to a temperature of about 40°–50° C. using an IR lamp (the solution was protected from the light, however) to help dissolve the materials in the N-methyl pyrrolidone.

Fiber optic bundles were prepared according to Example 2, using this overcoating precursor solution. The overcoated bundles were then tested according to the method of Example 2. The results are listed in Table 3.

TABLE 3

|  | Time to 63% signal change (seconds) | Time to 90% signal change (seconds) |
|---|---|---|
| Without overcoat | 34 | 64 |
| With overcoat | 192 | 248 |

Once again, the response time had been increased by the overcoat, but it was within the range suitable for indwelling catheter sensing.

EXAMPLE 5

This example demonstrates the present invention using a hydrophilic monomer (N-vinyl pyrrolidone) and a hydrophobic polymer (polyurethane) with a solvent (N-methyl pyrrolidone). A solution was prepared by mixing 33% by weight of N-vinyl pyrrolidone, 27% by weight of polyurethane (a polyurethane similar to that prepared by the method described in U.S. Pat. No. 4,024,871, Example 1, manufactured by Minnesota Mining and Manufacturing Company, St. Paul, Minn., with the following exceptions: a polytetramethylene ether glycol of molecular weight about 2000 was used; 1.9 moles of diisocyanate per mole of polyether glycol were held at a temperature of 80°–100° C.; the isocyanate terminated polyether in N,N-dimethylacetamide contained 14% solids; 3 mole-% diethylamine was used; the mixture was held at a temperature of about 55° F. (13° C.) for about 1 hour; the resultant solution of segmented polyurethane contained about 18% solids; the polymer had an intrinsic viscosity of 0.68 in dimethylacetamide at a concentration of 0.6 gram per 100 ml of solution); and 40% by weight of N-methyl pyrrolidone. To this was added 10% diallyl maleate and 4% DAROCURE 1173 photoinitiator, both of which were based on the weight of N-vinyl pyrrolidone. This precursor solution was prepared with warming to a temperature of about 40–50° C. using an IR lamp (the solution was protected from the light, however) to help dissolve the materials in the N-methyl pyrrolidone.

Fiber optic bundles were prepared according to Example 2, with the following exceptions. The mold was soaked in a solution of 45% by weight N-vinyl pyrrolidone, 55% by weight N-methyl pyrrolidone, and 0.5% by weight DAROCURE 1173 based on the N-methyl pyrrolidone. The overcoating precursor solution was then placed in the mold. The polymerization environment was oxygen-free due to the use of a glove bag, a nitrogen atmosphere, and a quartz sleeve around the tip of the mold. The mold was not placed in a low temperature bath after irradiation. After being removed from the mold, the gel-coated bundle was exposed to 25° C. water to exchange the NMP with water. The overcoated bundles were then tested according to the method of Example 2. The results are listed in Table 4.

TABLE 4

|  | Time to 63% signal change (seconds) | Time to 90% signal change (seconds) |
| --- | --- | --- |
| Without overcoat | 28 | 46 |
| With overcoat | 124 | 194 |

Once again, the response time had been increased by the overcoat, but it was within the range suitable for indwelling catheter sensing.

Using this composition, films were prepared as described in Example 1 for tensile testing to determine the strength of the material. The films were placed in 20°–25° C. water to exchange out the liquid portion and then placed in water for storage prior to testing. The tensile test samples were prepared and tested as described in Example 2. The tensile strength of the films made using this composition was 966 psi (6660 kPa) (average of 4 samples).

EXAMPLE 6

Fiber optic bundles were prepared according to Example 5, with the following exceptions. The mold was soaked in a solution of 65% by weight N-vinyl pyrrolidone, 35% by weight N-methyl pyrrolidone, and 0.5% by weight DAROCURE 1173 photoinitiator, the latter of which was based on the weight of N-vinyl pyrrolidone. The gel-coated bundle was air dried for 17 hours at room temperature (20°–25° C.). The dried coated bundle was placed in 25° C. water to exchange the NMP with water. The overcoated bundles were then tested according to the method of Example 2. The results are listed in Table 5.

TABLE 5

|  | Time to 63% signal change (seconds) | Time to 90% signal change (seconds) |
| --- | --- | --- |
| Without overcoat | 42 | 60 |
| With overcoat | 130 | 204 |

Once again, the response time had been increased by the overcoat, but it was within the range suitable for indwelling catheter sensing.

EXAMPLE 7

This example demonstrates the present invention using a hydrophilic monomer (N-vinyl pyrrolidone) and a hydrophobic monomer (benzyl acrylate) with a solvent (N-methyl pyrrolidone). A solution was prepared by mixing 38% by weight of N-vinyl pyrrolidone, 26% by weight of benzyl acrylate, 36% by weight of N-methyl pyrrolidone. To this was added 1.0% by weight of DAROCURE 1173 photoinitiator and 1% by weight of diallyl maleate, both of which were based on the weight of N-vinyl pyrrolidone and benzyl acrylate. This overcoat precursor solution was protected from light.

Using this overcoat precursor solution, fiber optic bundles were prepared according to Example 5, except that the mold was soaked in a solution of 65% by weight N-vinyl pyrrolidone, 35% by weight N-methyl pyrrolidone, and 0.5% DAROCURE 1173 photoinitiator, the latter of which was based on the weight of N-vinyl pyrrolidone. The overcoated bundles were then tested according to the method of Example 2. The results are listed in Table 6.

TABLE 6

|  | Time to 63% signal change (seconds) | Time to 90% signal change (seconds) |
| --- | --- | --- |
| Without overcoat | 42 | 68 |
| With overcoat | 104 | 178 |

Once again, the response time had been increased by the overcoat, but it was within the range suitable for indwelling catheter sensing.

EXAMPLE 8

This example demonstrates the present invention using a hydrophilic polymer [poly(N-vinyl pyrrolidone)] and a hydrophobic monomer (benzyl acrylate) with a solvent (N-methyl pyrrolidone). A solution was prepared by mixing 35% by weight of K-30 poly(N-vinyl pyrrolidone) (commercially available from BASF Corp., Chemicals Division, Parsippany, N.J.), 28% by weight of benzyl acrylate, and 37% by weight of N-methyl pyrrolidone. To this was added 1.0% by weight DAROCURE 1173 photoinitiator and 5% 1,6-hexanediol diacrylate, both of which were based on the weight of benzyl acrylate. This overcoat precursor solution was prepared with warming to a temperature of about 40°–50° C. using an IR lamp (the solution was protected from the light, however) to help dissolve the materials in the N-methyl pyrrolidone.

Using this overcoat precursor solution, fiber optic bundles were prepared according to Example 5, except that the mold was not presoaked. The overcoated bundles were then tested according to the method of Example 2. The results are listed in Table 7.

TABLE 7

|  | Time to 63% signal change (seconds) | Time to 90% signal change (seconds) |
| --- | --- | --- |
| Without overcoat | 44 | 72 |
| With overcoat | 74 | 130 |

Once again, the response time had been increased by the overcoat, but it was within the range suitable for indwelling catheter sensing.

EXAMPLE 9

A solution was prepared by mixing 32% by weight of N-vinyl pyrrolidone, 28% by weight of polysulfone UDEL 1700 (Amoco, Ridgefield, Conn.) and 40% by weight of N-methyl pyrrolidone (NMP) and 4% Darocure 1173 based on the weight of N-vinyl pyrrolidone. To this was added 2% diallyl maleate based on the weight of N-vinyl pyrrolidone. The solution was protected from light. Films were produced as in Example 1 using 20°–25° C. water to exchange the NMP with water and tested for tensile strength as in Example 2. Tensile strength of the films was 1288 psi (8881 kPa) (average of four samples). Permeability of the films was tested by wrapping them around the end of a pH sensor and evaluating the response time in an analogous manner to that described in Example 2. The results demonstrated that the films were acceptably permeable to hydrogen ions.

EXAMPLE 10

A solution was prepared by mixing 32% by weight of N-vinyl pyrrolidone, 28% by eight of polyethersulfone Ultrex 4100G (ICI Americas) and 40% by weight of N-methyl pyrrolidone (NMP) and 4% Darocure 1173 based on the weight of N-vinyl pyrrolidone. To this was added 2% diallyl maleate based on the weight of N-vinyl pyrrolidone. The solution was protected from light. Films were produced as in Example 1 using 20°–25° C. water to exchange the NMP with water and tested for tensile strength as in Example 2. Tensile strength of the films was 875 psi (6033 kPa) (average of four samples). Permeability of the films was tested by wrapping them around the end of a pH sensor and evaluating the response time in an analogous manner to that described in Example 2. The results demonstrated that the films were acceptably permeable to hydrogen ions.

The disclosures of all patents and publications cited herein are incorporated by reference. While this invention has been described in connection with specific embodiments, it should be understood that it is capable of further modification. The claims herein are intended to cover those variations which one skilled in the art would recognize as the chemical equivalent of what has been described herein. Thus, various omissions, modifications, and changes to the principles described herein may be made by one skilled in the art without departing from the true scope and spirit of the invention which is indicated by the following claims.

What is claimed is:

1. A method for making a shaped permeable polymeric material, the method comprising:
   (a) preparing a crosslinkable composition comprising a hydrophobic portion and a hydrophilic portion, wherein the hydrophobic portion is a polymeric material selected from the group consisting of a polysulfone, a polyethersulfone, a polyarylsulfone, a polyimide, a polyarylate, a cellulose acetate, a polyurethane, a polycarbonate, a polyester carbonate a phenoxy resin, a polyether imide, a cellulose acetate butyrate, a nylon, a polyvinyl butyral, a polyarylene oxide, a poly(urea urethane), a polyphenyl quinoxaline, and mixtures thereof;
   (b) placing the crosslinkable composition in a mold;
   (c) gelling the crosslinkable composition to form a shaped gelled composition comprising a hydrophobic portion, a hydrophilic portion, and a liquid portion; and
   (d) exchanging the liquid portion with an exchange liquid to form a shaped permeable polymeric material having a tensile strength, when fully hydrated, of at least about 525 psi (3620 kPa).

2. The method of claim 1 wherein the step of gelling the crosslinkable composition is carded out in an oxygen-reduced environment.

3. The method of claim 1 further including a step of exposing the shaped gelled polymeric composition to a humid atmosphere prior to the step of exchanging the liquid portion with an exchange liquid.

4. The method of claim 1 wherein the mold is presoaked prior to placing the crosslinkable composition in the mold.

5. The method of claim 1 wherein the crosslinkable composition further includes a crosslinking agent.

6. A method for making a coated blood gas sensor, the method comprising:
   (a) preparing a crosslinkable composition comprising a hydrophobic portion and a hydrophilic portion, wherein the hydrophobic portion of the crosslinkable composition comprises a hydrophobic polymeric material;
   (b) placing the crosslinkable composition and a portion of the sensor in a mold;
   (c) gelling the crosslinkable composition to form a shaped gelled composition comprising a hydrophobic portion, a hydrophilic portion, and a liquid portion; and
   (d) exchanging the liquid portion with an exchange liquid to form a shaped permeable polymeric material coated on the sensor having a tensile strength, when fully hydrated, of at least about 650 psi (4482 kPa).

7. The method of claim 6 wherein the hydrophilic portion of the crosslinkable composition comprises a hydrophilic monomeric material and the step of gelling comprises polymerizing at least a portion of the hydrophilic monomeric material and crosslinking the composition to form the shaped gelled composition.

8. The method of claim 7 wherein the liquid portion comprises an organic solvent.

9. The method of claim 7 wherein the hydrophilic monomeric material comprises N-vinyl pyrrolidone and the hydrophobic polymeric material comprises polyurethane or poly(urea urethane).

10. The method of claim 6 wherein the hydrophilic portion of the crosslinkable composition comprises a hydrophilic polymeric material and the step of gelling comprises crosslinking at least a part of the hydrophobic or hydrophilic polymeric materials.

11. The method of claim 10 wherein the liquid portion comprises an organic solvent.

12. The method of claim 1 wherein the hydrophilic portion of the crosslinkable composition comprises a hydrophilic monomeric material and the step of gelling comprises polymerizing at least a portion of the monomeric material and crosslinking the composition to form the shaped gelled composition.

13. The method of claim 12 wherein the liquid portion comprises an organic solvent.

14. The method of claim 1 wherein the hydrophobic and hydrophilic portions of the crosslinkable composition are part of a semihydrophilic polymer.

15. The method of claim 1 wherein the exchanging step comprises contacting the shaped gelled composition with a vapor of the exchange liquid.

16. A method for making a shaped permeable polymeric material, the method comprising:
   (a) preparing a crosslinkable composition comprising a hydrophobic polymeric material, a hydrophilic monomeric material, and an organic solvent, wherein the hydrophobic polymeric material is selected from the group consisting of a polysulfone, a polyethersulfone, a polyarylsulfone, a polyimide, a polyarylate, a cellulose acetate, a polyurethane, a polycarbonate, a polyester carbonate, a phenoxy resin, a polyether imide, a cellulose acetate butyrate, a nylon, a polyvinyl butyral, a polyarylene oxide, a poly(urea urethane), a polyphenyl quinoxaline, and mixtures thereof;

(b) placing the crosslinkable composition in a mold;

(c) gelling the crosslinkable composition to form a shaped gelled composition comprising a hydrophobic portion, a hydrophilic portion, and a liquid portion; and (d) exchanging the liquid portion with an exchange liquid to form a shaped permeable polymeric material having a tensile strength, when fully hydrated, of at least about 525 psi (3620 kPa).

17. The method of claim 16 wherein the organic solvent is selected from the group consisting of N-methyl pyrrolidone, N,N-dimethyl formamide, and N,N-dimethyl acetamide.

18. The method of claim 16 wherein the crosslinkable composition further includes a crosslinking agent.

19. The method of claim 18 wherein the crosslinkable composition further includes an initiator.

20. The method of claim 16 wherein the hydrophilic monomeric material of the crosslinkable composition is selected from the group consisting of N-vinyl pyrrolidone, N,N-dimethyl acrylamide, N-vinyl-N-methyl acetamide, N-vinyl valerolactam, N-vinyl caprolactam, acrylamide, acrylic acid, hydroxy ethyl acrylate, hydroxy ethyl methacrylate, poly(ethylene glycol) methyl ether acrylate, and mixtures or copolymers thereof.

21. The method of claim 20 wherein the hydrophilic portion of the crosslinkable composition comprises N-vinyl pyrrolidone and the hydrophobic portion of the crosslinkable composition comprises poly(urethane) or poly(urea urethane).

22. A method for making a shaped permeable polymeric material, the method comprising:

(a) preparing a crosslinkable composition comprising a hydrophobic portion and a hydrophilic portion, wherein the hydrophobic portion is a polymeric material selected from the group consisting of a polysulfone, a polyethersulfone, a polyarylsulfone, a polyimide, a polyarylate, a cellulose acetate, a polyurethane, a polycarbonate, a polyester carbonate, a phenoxy resin, a polyether imide, a cellulose acetate butyrate, a nylon, a polyvinyl butyral, a polyarylene oxide, a poly(urea urethane), a polyphenyl quinoxaline, and mixtures thereof;

(b) placing the crosslinkable composition in a mold;

(c) gelling the crosslinkable composition to form a shaped gelled composition comprising a hydrophobic portion, a hydrophilic portion, and a liquid portion;

(d) evaporating the liquid portion; and (e) adding an exchange liquid to form a shaped permeable polymeric material having a tensile strength, when fully hydrated, of at least about 525 psi.

23. The method of claim 22 wherein the crosslinkable composition further includes an organic solvent.

24. The method of claim 23 wherein the hydrophilic portion of the crosslinkable composition comprises N-vinyl pyrrolidone and the hydrophobic portion of the crosslinkable composition comprises poly(urethane) or poly(urea urethane).

25. A method for making a coated blood gas sensor, the method comprising:

(a) preparing a crosslinkable composition comprising a hydrophobic portion and a hydrophilic portion;

(b) placing the crosslinkable composition and a portion of the sensor in a mold;

(c) gelling the crosslinkable composition to form a shaped gelled composition comprising a hydrophobic portion, a hydrophilic portion, and a liquid portion; and (d) exchanging the liquid portion with an exchange liquid to form a shaped permeable polymeric material coated on the sensor having a tensile strength, when fully hydrated, of at least about 525 psi.

26. The method of claim 25 wherein the blood gas sensor comprises a pH sensor, a $CO_2$ sensor, and an $O_2$ sensor.

27. The method of claim 25 wherein the gelling step is performed in an oxygen-reduced environment.

28. The method of claim 25 wherein the crosslinkable composition further includes an organic solvent.

29. The method of claim 28 wherein the hydrophobic portion of the crosslinkable composition is selected from the group consisting of a polysulfone, a polyethersulfone, a polyarylsulfone, a polyimide, a polyarylate, a cellulose acetate, a polyurethane, a polycarbonate, a polyester carbonate, a phenoxy resin, a silicone, a polyether imide, a cellulose acetate butyrate, a nylon, a polyvinyl butyral, a polyarylene oxide, a poly(urea urethane), a polyphenyl quinoxaline, and mixtures thereof.

30. The method of claim 29 wherein the hydrophilic portion of the crosslinkable composition is selected from the group consisting of N-vinyl pyrrolidone, N,N-dimethyl acrylamide, N-vinyl-N-methyl acetamide, N-vinyl valerolactam, N-vinyl caprolactam, acrylamide, acrylic acid, hydroxy ethyl acrylate, hydroxy ethyl methacrylate, poly (ethylene glycol) methyl ether acrylate, and mixtures or copolymers thereof.

31. The method of claim 1, wherein the method further includes a step of placing a portion of a blood gas sensor in the mold, and wherein the shaped permeable polymeric material is coated on the sensor.

32. The method of claim 7, wherein the method further includes a step of placing a portion of a blood gas sensor in the mold, and wherein the shaped permeable polymeric material is coated on the sensor.

33. The method of claim 9, wherein the method further includes a step of placing a portion of a blood gas sensor in the mold, and wherein the shaped permeable polymeric material is coated on the sensor.

34. The method of claim 20, wherein the method further includes a step of placing a portion of a blood gas sensor in the mold, and wherein the shaped permeable polymeric material is coated on the sensor.

35. The method of claim 24, wherein the method further includes a step of placing a portion of a blood gas sensor in the mold, and wherein the shaped permeable polymeric material is coated on the sensor.

36. The method of claim 5 wherein the permeable polymeric material has a tensile strength, when fully hydrated, of at least about 800 psi.

37. The method of claim 5 wherein the crosslinking agent comprises diallyl maleate.

38. The method of claim 16 wherein the permeable polymeric material has a tensile strength, when fully hydrated, of at least about 800 psi.

39. A method for making a coated blood gas sensor, the method comprising:

(a) preparing a crosslinkable composition comprising a hydrophobic portion selected from the group consisting of a polysulfone, a polyethersulfone, a polyarylsulfone, a polyimide, a polyarylate, a cellulose acetate, a polyurethane, a polycarbonate, a polyester carbonate, a phenoxy resin, a silicone, a polyether imide, a cellulose acetate butyrate, a nylon, a polyvinyl butyral, a polyarylene oxide, a poly(urea urethane), a polyphenyl quinoxaline, and mixtures thereof, and a hydrophilic portion selected from the group consisting of N-vinyl pyrrolidone, N,N-dimethyl acrylamide, N-vinyl-N-methyl acetamide, N-vinyl valerolactam, N-vinyl caprolactam, acrylamide, acrylic acid, hydroxy ethyl acrylate, hydroxy ethyl methacrylate, poly(ethylene glycol) methyl ether acrylate, and mixtures or copolymers thereof;

(b) placing the crosslinkable composition and a portion of the sensor in a mold;

(c) gelling the crosslinkable composition to form a shaped gelled composition comprising a hydrophobic portion, a hydrophilic portion, and a liquid portion; and (d) exchanging the liquid portion with an exchange liquid to form a shaped permeable polymeric material coated on the blood gas sensor.

* * * * *

UNITED STATES PATENT AND TRADEMARK OFFICE
CERTIFICATE OF CORRECTION

PATENT NO.: 5,670,097
DATED: September 23, 1997
INVENTOR(S): Daniel C. Duan, Mark S. Schaberg, Terence M. Fogarty, William L. Howard, Jr., and Kenneth B. Wood It is certified that error appears in the above-identified patent and that said Letters Patent is hereby corrected as shown below:

Col. 4, line 57, "20°1425°" should read -- 20°-25° --.

Col. 6, line 5, "mount" should read -- amount --.

Col. 6, line 57, "590" should read -- 5-90 --.

Col. 10, line 13, "carded" should read -- carried --.

Col. 11, line 51, "coveting" should read -- covering --.

Col. 11, line 57, "carded" should read -- carried --.

Col. 11, line 60, "20°1425°" should read -- 20°-25° --.

Col. 11, line 64, "20°1425°" should read -- 20°-25° --.

Col. 12, line 48, "Coming" should read -- Corning --.

Col. 12, line 63, "20°1425°" should read -- 20°-25° --.

UNITED STATES PATENT AND TRADEMARK OFFICE
CERTIFICATE OF CORRECTION

PATENT NO. : 5,670,097
DATED : September 23, 1997
INVENTOR(S) : Daniel C. Duan, Mark S. Schaberg, Terence M. Fogarty, William L. Howard, Jr., and Kenneth B. Wood It is certified that error appears in the above-identified patent and that said Letters Patent is hereby corrected as shown below:

Col. 14, line 9, After the table, insert -- Once again, the response time had been increased by the overcoat, but it was within the range suitable for indwelling catheter sensing. --

Col. 17, line 64, "carded" should read -- carried --.

Signed and Sealed this

Second Day of February, 1999

Attest:

Attesting Officer

*Acting Commissioner of Patents and Trademarks*